United States Patent [19]
Li et al.

[11] Patent Number: 5,726,203
[45] Date of Patent: Mar. 10, 1998

[54] QINGHAOSU DERIVATIVES AGAINST AIDS

[76] Inventors: Zelin Li, Institute of Chinese Material Medica, Chinese Academy of Traditional Chinese Medicine, Dongzhimennei, Beijing 100700; Xuande Luo, 9-3-105 Baijiazhuangxiii, Chaowal, Beijing 100020; Yi Zeng, 100, Yingxinjie, Xuanwu District, Beijing 100052; Lin Ma, Ximen 1401, No. 2, Yabaolu, Chaoyan District, Beihing 100020, all of China

[21] Appl. No.: 581,629

[22] PCT Filed: Jul. 19, 1994

[86] PCT No.: PCT/CN94/00056

§ 371 Date: May 21, 1996

§ 102(e) Date: May 21, 1996

[87] PCT Pub. No.: WO95/03311

PCT Pub. Date: Feb. 2, 1995

[30] Foreign Application Priority Data

Jul. 19, 1993 [CN] China ............... 93108651.5

[51] Int. Cl.[6] .............. A61K 31/335; C07D 323/04
[52] U.S. Cl. .............. 514/450; 549/348; 549/354; 549/358
[58] Field of Search .............. 549/348, 354, 549/358; 514/450

[56] References Cited

U.S. PATENT DOCUMENTS

| | | | |
|---|---|---|---|
| 4,816,478 | 3/1989 | Thornfeldt | 514/450 |
| 5,171,676 | 12/1992 | Ziffer et al. | 435/124 |

OTHER PUBLICATIONS

Luo et al, "Helvetica Chimica. Acta", vol. 67, pp. 1515–1521, 1984.

*Primary Examiner*—Ba K. Trinh
*Attorney, Agent, or Firm*—Loeb & Loeb LLP

[57] ABSTRACT

This invention relates to the compounds represented by general formula (I) and the processes for their preparation, wherein R is selected from $C_1$–$C_4$ alkyl, $C_3$–$C_6$ cycloalkyl, phenyl unsubstituted or substituted by a halogen atom or nitro group, biphenyl unsubstituted by a halogen atom or nitro group, naphthyl unsubstituted or substituted by a halogen atom or nitro group. The compounds of this invention are used to prepare agents for prevention and treatment of AIDS and drugs against malaria and toxoplasmosis.

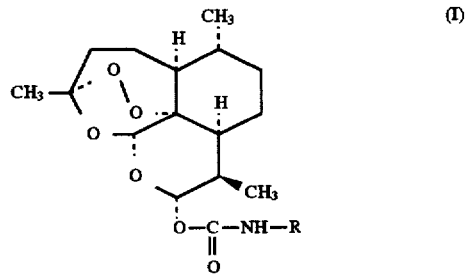

15 Claims, No Drawings

QINGHAOSU DERIVATIVES AGAINST AIDS

This is a 371 application of PCT/CN 94/00056 dated Jul. 19, 1994 publshied as WO95/03311 Feb. 2, 1995.

FIELD OF THE INVENTION

This invention relates to carbocyclic compounds, in particularly to artemisinin-type new derivatives, their preparation and use in prevention and treatment of AIDS viruses.

BACKGROUND OF THE INVENTION

AIDS is the abbreviation of acquired immunodeficeincy syndrom. In 1981, the first case of AIDS was found in the United States of America. In 1983, Professor Montagnier of the Pasteur institute, France, isolated for the first time a virus from a patient's blood, which was later designated as HIV, there by this disease, AIDS, was proved to be a viral infectious disease characterized by acquired immunodeficiency. Since HIV is T-lymphocytophilic, on one hand it multiplies and releases continuously in these cells and the released virus again invades new T4-lymphocytes; on the other hand, the T4-lymphocytes invaded by this virus may coalesce with other T4-lymphocytes to form syncytia which are unstable and may die easily. The virus multiplies, releases, forms syncytia and dies repeatedly as such, thereby results in profound cellular immunodeficiency, finally destroys human immune function and leads to death. Besides T-lymphocytes, HIV may also invade macrophages, B-lymphocytes, etc., especially it may form chronic infection in macrophages, and may exist for a long time. The development of this disease may be divided into three stages, i.e., HIV-carrier stage, ARC stage and AIDS stage. Once the disease developed to AIDS stage, it progresses rapidly and the 3-year survival rate is less than 10%. At present, approximately 20,000,000 persons are infected by HIV in the world, the number of AIDS patients reached 600,000 and half of them have already died. China is not an exception. AIDS was imported into China in 1984. At present, 890 persons infected by HIV have been found in China among them, 740 HIV-carriers and 5 AIDS patients are Chinese. The number of HIV-infected persons is still continuously increasing.

With regard to anti-HIV agents, the first one reported was Suramin. In 1985, AZT (3'-azido-3'-deoxythymidine), etc., were found to possess anti-HIV activity in vitro. Clinical studies were carried out in 1986, and AZT was approved by FDA of the United States of America as the first drug to be used for the treatment of AIDS in 1987. Up to now, several hundred new compounds and their prescriptions including dozens of natural products and traditional Chinese medicine have been screened in the world. Only AZT, DDI (di-deoxytrophicardyl) and DDC (di-deoxycytidine) are approved by the FDA of the United States of America to be used for the treatment of AIDS; among natural products and traditional Chinese medicinal herbs, such as trichosanthin is approved by the FDA for clinical observation. But all these drugs have different types of toxicity, for example, 4–6 weeks after the use of AZT, inhibition of bone marrow appears, then severe anemia develops; 6 months after the use of AZT alone, drug resistance may be produced; furthermore AZT does not exert inhibitory effect on the virus within infected macrophages thus it cannot remove the hidden peril, and, in addition, its price is high. DDC and DDI produce toxicity to peripharal nerves which appears 6 weeks after drug administration; higher dostage may result in sequelae which may still be present even one year after discontinuation of the drug. Trichosanthin has produced neurotoxicity in clinical trial, and in severe cases temporary dementia and even coma appeared. Experimental studies showed that treatment of HIV-infected macrophages with trichosanthin produced and released a soluble toxic substance which might exert serious destructive effect to human brain cells.

Up to now, experimenal studies and evaluation have been carried out with several hundred drugs and their prescriptions, natural products, single traditional Chinese drugs and composite traditional Chinese drugs in the world. Effective components were seperated from only very few of them, such as glycyrrhizim and lentinam reported from Japan, and effective component of Viola yedoensis reported from the University of California, USA, etc. Most of the compounds were nucleosides, adenosines or peptide derivatives. Whereas, crude extracts were used in experiments conducted on the majority of these drugs. Up to the world congress of AIDS held in Amsterdam, the Netherlands in 1992, the breakthrough progress in drug research was still not seen.

SUMMARY OF THE INVENTION

The object of the present invention is to provide an anti-AIDS agent with low toxicity, low price, and to overcome the shortcomings in the prior art.

Another object of the present invention is to provide a prosess for preparation of the above-mentioned agent.

Still another object of the present invention is to provide a use of the agent, in particular, the use as an anti-AIDS agent.

The object of the invention was attained as such:

This invention relates to the compounds represented by general formula (I) and their pharmaceutical acceptable salt.

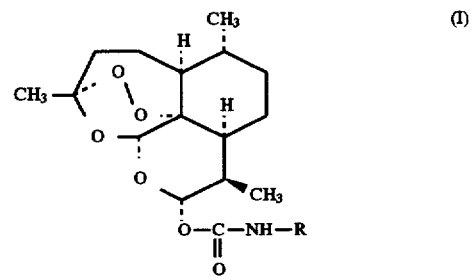

wherein R is selected from $C_1$–$C_4$ alkyl, $C_3$–$C_6$ cycloalkyl, phenyl unsubstituted or substituted by a halogen atom or nitro group, biphenyl unsubstituted or substituted by a halogen atom or nitro group, naphthyl unsubstituted or substituted by a halogen atom or nitro group.

Among the compounds represented by formula (I), the representive compounds includes: dihydroqinghaosu-methylcarbamate; dihydroqinghaosu-ethylcarbamate; dihydroqinghaosu-propylcarbamate; dihydroqinghaosu-butylcarbamate; dihydroqinghaosu-cyclohexylcarbamate; dihydroqinghaosu-benzenecarbamate; dihydroqinghaosu-m-chlonobenzenecarbamate; dihydroqinghaosu-p-chlonobenzenecarbamate; dihydroqinghaosu-p-bromobenzenecarbamate; dihydroqinghaosu-p-nitrobenzenecarbamate; dihydroqinghaosu-p-biphenylcarbamate; dihydroqinghaosu-1-naphthylcarbamate.

The present invention also relates to a process for preparation of the compounds represented by general formula (I), comprising following steps:

adding isocyanates into dihydroqinghaosu dissolved in dichloromethane, with the molar ratio (mol/mol) of dihydroqinghaosu to isocyanates being 1:1 to 1:2, to obtain a reaction solution;

reflexing the reaction solution for 1-3 days with stirring;

filting and evaporating the reaction solution to obtain a solid product;

chromatographing the solid product on silica gel column by using a mixture of petroleumether and ethylacetate with a volume ratio of petroleumether to ethyl acetate being 5:5-9:1;

collecting the required fraction, removing solvent and obtaining crystals.

In the above process, said isocyanates includes alkylcarbamate, benzenecarbamate, cyclohexylcarbamate, biphenylcarbamate and naphthylcarbamate.

The present invention also relates to a composition comprising said compound, uses of said compound for preparing agents for prevention and treatment of AIDS, anti-malarial and anti-toxoplasma.

The present invention has following advantages:

1. Compounds according to the present invention have a higher inhibition and killing effect to HIV virus with low toxicity to both animal and human being.

2. Compounds according to the present invention not only have effect on HIV in T-lymphocytes but also have obvious effect on HIV in macrophages.

In other words, a traditional Chinese herb, *Artemisia annua*. L., with abundant resources in China was used in the present invention. Qinghaosu (Artemisinin) was extracted from *Artemisia annua* L. A breakthrough progress has been made in the anti-HIV effect of its serial derivatives, thereby the object of the invention was accomplished.

Following is a detail description to the present invention.

Qinghaosu (Artemisinin), extracted from *Artemisia annua*. L. firstly in China, is a noval anti-malarial agent which is a sesquiterpene lactone comprising a peroxide bridge. Various of its derivatives are all derived from dihydroqinghaosu.

Following is a detail description of the present invention.

This invention relates to the compounds represented by general formula (I) and their pharmaceutical acceptable salt,

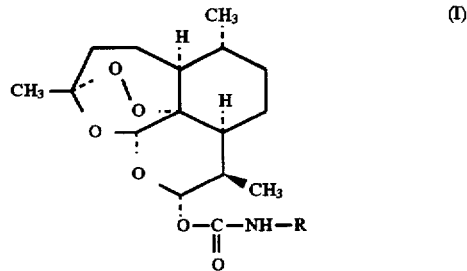

wherein R is selected from $C_1$-$C_4$ alkyl, $C_3$-$C_6$ cycloalkyl, phenyl unsubstituted or substituted by a halogen atom or nitro group, biphenyl unsubstituted or substituted by a halogen atom or nitro group, naphthyl unsubstituted or substituted by a halogen atom or nitro group.

A process for preparation of the compounds represented by general formula (I) employed in the present invention comprising following steps:

adding isocyanates into dihydroqinghaosu dissolved in dichloromethane, with the molar ratio (mol/mol) of dihydroqinghaosu to isocyanates being 1:1 to 1:2, to obtain a reaction solution;

reflexing the reaction solution for 1-3 days with stirring;

filting and evaporating the reaction solution to obtain a solid product;

chromatographing the solid product on silica gel column by using a mixture of petroleumether and ethyl acetate with a volume ratio of petroleumether to ethylacetate being 5:5-9:1;

collecting the required fraction, removing solvent and obtaining crystals.

In the above process, said isocyanates includes alkylcarbamate, benzenecarbamate, cyclohexylcarbamate, biphenylcarbamate and naphthylcarbamate. Thus, compounds and its pharmaceutical acceptable salt can be prepared. These compounds includes: dihydroqinghaosu-methylcarbamate; dihydroqinghaosu-ethylcarbamate; dihydroqinghaosu-propylcarbamate; dihydroqinghaosu-butylcarbamate; dihydroqinghaosu-cyclohexylcarbamate; dihydroqinghaosu-benzenecarbamate; dihydroqinghaosu-m-chlonobenzenecarbamate; dihydroqinghaosu-p-chlonobenzenecarbamate; dihydroqinghaosu-p-bromobenzenecarbamate; dihydroqinghaosu-p-nitrobenzenecarbamate; dihydroqinghaosu-p-biphenylcarbamate; dihydroqinghaosu-1-naphthylcarbamate.

In the process, dichloromethane, whose concentration is well-known in the art, such as 99.0%, can be employed to dissolve dihydroqinghaosu.

Above compounds can be used as a drug alone or in a pharmaceutical composition. In the composition, it contains 0.1-99.5%, preferably, 0.5-90% of the compound, and other pharmaceutical acceptable inactive carriers with low toxicity to human and animal.

Said carriers are one or several kind of diluent, filler or adjuvant in solid, semisolid or liquid form, it is suggested that the dosage in the pharmaceutical composition to be administrated is measured by per kilogram of body weight. The compounds of the present invention can be used by intravenous, bonemarrow, rectal, oral, intramuscular or hypedermic administration, oral administration is preferred.

The oral preparation are in solid or liquid form such as powder, tablet, capsule, granule, suspension, drops, syrup and preparation for hypo-tongue administration.

The dosage of the compounds of the present invention is according to the situation of patient (age and body weight), route of administration, type of disease and stage of disease and so on. Usually, the effective dose of these compounds is 0.5-1.5 mg, preferably, 0.6-1 mg per day.

THE BEST MODE TO CARRY OUT THE INVENTION

The pharmacologic and toxicologic studies of the compounds according to the present invention were illustrated as following.

EXPERIMENT 1. ANTI-HIV EXPERIMENT

A. Effect on $MT_4$ cells

1. Materials

The virus used was HIV-1 which had been obtained from Professor Montagnier of the Pastear Institute, France. The virus titer used in the experiment was $1\times10^4$ $TCID_{50}$/ml. The cell culture used was CEM cell line which was cultivated in the HIV laboratory of Institute of Virology, Chinese Academy of Preventive Medicine, for cultivation storage of HIV-1.

The compounds used in the experiment were qinghaosu, dihydroqinghaosu, Artesunate, Artemether, dihydroqinghaosu-methylcarbamate, dihydroqinghaosu-benzenecarbamate, qinghaosu-morpholinyl propylether maleate, dihydroqinghaosu-diethyl amino ethyl ether maleate, deoxyqinghaosu-morpholinyl ethyl ether maleate, qinghaosu-morpholinyl propanol ether maleate, qinghaosu-3,5-dimonpholinyl methyl-4-hydroxy benzyl ether maleate, dihydroqinghaosu-m-chlorobenzoate, qinghaosu-3-pyrrolidinylmethyl-4-hydroxybenzoate oxalate, and qinghaosu-3-morpholinylmethyl-4-hydroxybenzoate oxalate. AZT was used as a positive control. The concentration of the original solution of these compounds were all 1 mg/ml.

2. Method a. Freshly cultured MT4 cells ($5 \times 10^5$/ml) were co-cultivated with the virus fluid ($10^3$ $TCID_{50}$/ml) in a $CO_2$ incubator at 37° C. for 1–1.5 hours. RPMI 1640 complete medium (containing 10% Bovine serum and antibiotics, such as penicillin) was used to wash the unbound virus.

Complete medium was added to correct the concentration for use.

The experiment was carried out on the plates with 96 wells. 0.1 ml of the above-mentioned infected MT4 cell suspension was added into each well, and then 0.1 ml of various concentrations of the drugs were added. A control group with AZT as a positive drug and a virus control without drug (with only virus-infected MT4 cells) were set up. Each concentration of the drugs was added into two wells. Both the experiment group and the control group were incubated in a $CO_2$ incubator at 37° C. The drug solution were changed 3 days later, and the following observations were carried out 6 days afterwards.

b. Observation on the growth situation of cells. Trypan blue dye was used to observe the quantity of live cells in each group.

c. Determination of the virus antigen expression. The immunoenzymatic method was used to examine the virus antigen expression. Cells from each group were separately smeared in two wells. They were fixed with cold acetone, HIV-positive serum was dropped into the wells. After incubated in a $CO_2$ incubator at 37° C. for 30 minutes, they were washed with PBS for 3 times. Enzyme-labelled SPA was dropped into the wells. They were incubated in the same condition for 30 minutes, washed with PBS for 3 times, and then put in substrate solution to stain for 2–3 minutes, washed with distilled water, and observed under microscope. Normal cells were colorless, whereas virus-carrying cells appeared browrish red.

3. Evaluation on Result

The virus control group on the smear showed many distinct browrish red cells. The AZT $1 \times 10^{-1}$, $1 \times 10^{-2}$, $1 \times 10^{-3}$ group showed entirely no pink cells, indicating that the method used was reliable. The mark used were as follows:

"–" indicates that positive cells were not seen in the whole well;

"±" indicates that there were only 1–2 doubtful positive cells in whole well;

"+" indicates that there were 2–3 or more positive cells in the whole well.

The experiment was repeated two to three times.

The concentration of the original fluid of these compounds were all 1 mg/ml. 0.1 ml was taken and added into 0.1 ml of virus-carrying cell suspension, thus the reaction concentrations were as follows: in the original fluid group, 0.1 mg/0.2 ml, i.e., 0.5 mg/ml; in $1 \times 10^{-1}$ group, 0.05 mg/ml; in $1 \times 10^{-2}$ group, 0.005 mg/ml; in $1 \times 10^{-3}$ group, 0.0005 mg/ml, i.e., 0.5 µg/ml; and on the analogy of this.

TABLE 1

Comparison on the effect on HIV-1 ($MT_4$) of the several compounds.

| Compound | Concentration | | | |
|---|---|---|---|---|
| | $1 \times 10^{-1}$ (50 µg/ml) | $1 \times 10^{-2}$ (5 µg/ml) | $1 \times 10^{-3}$ (0.5 µg/ml) | $1 \times 10^{-4}$ (0.05 µg/ml) |
| Qinghaosu | – | – | + | + |
| Dihydroqinghaosu | – | – | ± | + |
| Artesunate | – | – | – | + |
| Artemether | – | – | ± | + |
| Dihydroqinghaosu-methylcarbamate | – | – | – | – |
| Dihydroqinghaosu-benzenecarbamate | – | – | – | ± |
| AZT | – | – | – | / |
| Qinghaosu-morpholinyl propyl ether maleate | – | + | + | |
| Dihydroqinghaosu-diethylamino ethyl ether maleate | ± | + | + | |
| Deoxyquinghaosu-morpholinyl propanol ether maleate | – | + | – | |
| Qinghaosu-morpholinyl propanol ether maleate | + | + | + | |
| Qinghaosu-3,5-dimorpholinyl methyl-4-hydroxy benzyl ehter maleate | + | + | + | |
| Dihydroqinghaosu-m-chlorobenzoate | – | – | + | |
| Qinghaosu-3-pyrrolidinylmethyl-4-hydroxy benzoate oxalate | – | + | – | |
| Qinghaosu-3-morpholinyl methyl-4-hydroxy benzoate oxalate | ± | + | + | |

According to Table 1, representative compounds, dihydroqinghaosu-methylcarbamate and dihydroqinghaosu-benenecarbamate showed distinct inhibition on HIV.

B. Effect on U937 cells

Furthermore, a part of the compounds according to the present invention were used to test their inhibition effect on U937 cell line (macrophage cell line)according to the methods in Experiment 1. Then HIV-antigen and reverse transcriptase in cells were tested, results were shown in Table 2.

TABLE 2

Inhibition effect on U937 on a part of the compounds of the present invention.

| Compound and dosage | Cell line and Virus | Antigen test (IE) | Activity of reverse transcription (CPM) |
|---|---|---|---|
| Artesunate (50 µg/ml) | U937 HIV-1 | – | –(4846) |
| AZT (1 µg/ml) | U937 HIV-1 | + | +(10865) |
| Control | U937 HIV-1 | + | +(24502) |
| Dihydroqinghaosu-benzenecarbamate (50 µg/ml) | U937 HIV-1 | – | –(2305) |

TABLE 2-continued

Inhibition effect on U937 on a part of the compounds of the present invention.

| Compound and dosage | Cell line and Virus | Antigen test (IE) | Activity of reverse transcription (CPM) |
|---|---|---|---|
| Dihydroqinghaosu-methylcarbamate (50 µg/ml) | U937 HIV-1 | − | −(4463) |
| Control | U937 HIV-1 | + | +(24502) |

From Table 2, it is obvious that the compounds according to the present invention showed distinct inhibition on U937 infected HIV-1, whereas AZT does not show the inhibition.

EXPERIMENT 2. ANTIMALARIA EFFECT

Effect on Erythrocytic Stage of Plasmodium Berghei

1. "Four day inhibition test" in mice

To determinate the $SD_{50}$ with Peters' "four day inhibition test".

Hybrid Kunming strain mice, body weight 18–22 g, were inculated with $1 \times 10^7$ parasites infected RBC intraperitoneally on $D_0$. Dihydroqinghaosu-methylcarbamate, dihydroqinghaosu-butylcarbamate, dihydroqinghaosu-benzenecarbamate and dihydroqinghaosu-4-nitrobenzenecarbamate with different concentration were given once a day from $D_0$–$D_3$. Blood smears from mouse's tail were made on $D_4$, stained with Gimsa reagent and examined under microscope to count the infected and uninfected erthrocyte to get infected rate. Inhibitory rates of different dosages were calculated by following formula. The $SD_{50}$ was calculated by the simplified probit analysis:

Inhibitory rate =

$$\frac{\text{Infected rate of RBC in control group} - \text{Infected rate of RBC in drug treat group}}{\text{Infected rate of RBC in control group}} \times 100$$

Results is following:

TABLE 3

| compounds | $SD_{50}$ (mg/kg/day) |
|---|---|
| Dihydroqinghaosu-methylcarbamate | 0.24 |
| Dihydroqinghaosu-butylcarbamate | 0.25 |
| Dihydroqinghaosu-benzengcarbamate | 0.29 |
| Dihydroqinghaosu-4-nitrobenzenecarbamate | 0.30 |

EXPERIMENT 3. ANTITOXOPLASMA EFFECT

In vitro incubation was used in the experiment. Macrophages were taken from intraperitoneal of the uninfected BALB/C mice (obtained from Universite Pierre et Marie Curie), centrafuged, washed and counted. Around $1.28 \times 10^5$ cells was added into each culture dish, incubated at 37° C. for 3 hours to let the cells to be adherented, then infected by parasites (Toxoplasma Gendei, obtained from Universite Pierre et Marie Curie), in which parasite number was $1 \times 10_6$, so that there were 5 organisms per macrophage. The dishes were incubated at 37° C. for 48 hours, different concentration, (i.e., 50 µg/ml, 100 µg/ml, 200 µg/ml) of the compound according to the present invention was added in. In a control group, no drug was added in. After being cultured at 37° C. for 48 hours, dishes of compound treated groups and control group were colorated. Under microscope, the number of infected and uninfected macrophages in each dishes were counted and to calculated infected rate of macrophage and to count the number of parasites in 100 macrophages. Result showed that dihydroqinghaosu-methylcarbamate had obvious inhibition on Toxoplasma Gendei in vitro.

TABLE 4

Effect of dihydroqinghaosu-methylcarbamate on Toxoplasma Gendei in vitro.

| Dosage (µg/ml) | Infected rate of macrophages | Inhibition rate (%) | No. of parasites in 100 macrophages | Inhibition rate (%) |
|---|---|---|---|---|
| 50 | 0.67 | 99.1 | 2.67 | 99.5 |
| 100 | 0 | 100 | 0 | 100 |
| 200 | 0 | 100 | 0 | 100 |
| Control | 75.60 | | 544.00 | |

EXPERIMENT 4. TOXICALOGIC STUDY OF THE COMPOUNDS OF THE PRESENT INVENTION

Acute Toxicity in Mice

Animals: Hybrid swiss strain mice (provided by Animal House of Institute of Chinese Mateia Media, China Academy of Traditional Chinese Medicine), 20–22 grams, less than 6 weeks age of both sexes fed in laboretory for 3–5 days observation and a random taking food and drinking.

Drugs: Dihydroqinghaosu-methylcarbamate and dihydroqinghaosu-benzenecarbamate.

Above two drugs in powder form were dissolved into peanut oil. The biggest dose were 2000 mg/kg and 2161 mg/kg respectively. The distances between two dose groups were 0.7 and 0.68 respectively, with 5 dose groups each drugs.

Method: The mice were given single dose of above compound respectively intragastrically, the acute intoxication manifestrations were observed the LD value ($LD_5$, $LD_{50}$ and $LD_{95}$) and B value were determined by three days mortality.

Result: The symptoms and signs of acute intoxication were observed as following: inhibited activity, bad appetite, hair looseness, cardiac rate decreased then died. In large dose group, all mice died within three days, the LD and B value were 1065.89 mg/kg and 1120.84 mg/kg respectively. See Table 5 and 6 for detail.

Also, toxicity of compounds similar to the compound of the present invention was lower than that of Artemether, dihydroqinghaosu and Artesunate. See Table 7 for detail.

TABLE 5

Death distribution of mice.

| drugs | dosage (mg/kg) | female exp./death | male exp./death | female + male exp./death |
|---|---|---|---|---|
| Dihydroqinghaosu-benzenecarbamate | 2000 | 6/6 | 6/6 | 12/12 |
| | 1400 | 6/4 | 6/3 | 12/7 |
| | 980 | 6/2 | 6/2 | 12/4 |
| | 686 | 6/1 | 6/2 | 12/3 |

TABLE 5-continued

Death distribution of mice.

| drugs | dosage (mg/kg) | female exp./death | male exp./death | female + male exp./death |
|---|---|---|---|---|
| Dihydroqinghaosu-methylcarbamate | 480 | 6/0 | 6/1 | 12/1 |
| | 2161 | 5/5 | 5/5 | 10/10 |
| | 1470 | 5/2 | 5/3 | 10/5 |
| | 1000 | 5/2 | 5/2 | 10/4 |
| | 680 | 5/2 | 5/1 | 10/2 |
| | 462 | 5/0 | 5/1 | 10/1 |

TABLE 6

Acute toxicity in mice (LD) and slope (B).

| drugs | sex | $LD_5$ | $LD_{50}$ | $LD_{95}$ | B |
|---|---|---|---|---|---|
| Dihydroqinghaosu-benzendcarbamate | F | 603.91 | 1097.23 | 1993.51 | 6.343 |
| | M | 352.10 | 1039.73 | 3069.59 | 3.498 |
| | F + M | 463.33 | 1065.89 | 2452.08 | 4.546 |
| Dihydroqinghaosu-methylcarbamate | F | 543.17 | 1213.64 | 2711.67 | 4.711 |
| | M | 360.92 | 1028.85 | 2932.84 | 3.620 |
| | F + M | 435.75 | 1120.84 | 2883.02 | 4.01 |

TABLE 7

Comparasion of $LD_{50}$ of several similar compounds.

| drug | $LD_{50}$ (mg/kg) | Remarks* |
|---|---|---|
| Artemether | 263 | I.M. |
| Artesunate | 769 | I.V. |
| Dihydroqinghaosu | 765 | P.O. |
| Dihydroqinghaosu-benzenecarbamate | 1065 | P.O. |
| Dihydroqinghaosu-methylcarbamate | 1120 | P.O. |

*: Table 7,
I.M.: Intramuscular injection;
I.V.: Intravenous injection; and
P.O.: per os.

Subacute toxicologic study showed that basic safe dosages of dihydroqinghaosu-benzenecarbamate and dihydroqinghaosu-methylcarbamate were 54 mg/kg/day and 30.2 mg/kg/day respectively.

Follwings are general explanation of examples.

Melting points were taken on a Fisher-Johns melting point apparatus. Silica gel 60 (230–400 mesh ASTM) from Merck was used for column (Aldrich Chemical Co.). Optical rotations were measured with Perkin-Elmer-241-MC polarimeter in CHCl$_3$. UV spectra were measured in CHCl$_3$ with a Hewlett-Packard-8450-A spectrophotometer, $\lambda_{max}$) in log$\epsilon$) in nm. IR spectra (in cm$^{-1}$) were obtained on a Beckman-4230 instrument as KBr tablet or CHCl$_3$ solution between NaCl plates. Chemical ionization (CI) mass spectra (m/z) were obtained bu using a Finnigan-1015D spectrometer. $^1$H-NMR spectra were determined by using JEOL-FX-100 spectrometer and a Nicolet-500 spectrometer with Me$_4$Si as an internal reference (δ in ppm, J in Hz). Fraction of column chromatography was detected by thin layer chromatograph. And thin layer chromatography were performed on silica gel GF plate (10×20 cm) from Analtech, Inc., with petroleum ether/AcOEt; detection with iodine vapors.

EXAMPLE 1

Preprartion of Dihydroqinghaosu-Methylcarbamate

A solution of dihydroqinghaosu (284 mg, 1 mmol) in dry CH$_2$Cl$_2$ (6 ml) and methyl isocyanate (63 mg, 1.1 mmol) was refluxed for ca. 2 days. The solution was filtered and evaporated in vacuo at 40° C. to give a solid, which was chromatographed on a silica-gel column with petroleumether/AcOEt 8:2. The fraction obtained was evaporated to give a white powder (217.6 mg).

m.p. 175–177° C.; MS (CI, NH$_3$): 342 (M$^+$+ 1);
$^1$H NMR (CDCl$_3$) δ (ppm)
5.50 (s, 1H, C$_5$—H
5.77 (d, 1H, C$_{12}$—H
2.65 (m, 1H, C$_{11}$—H)
Anal. Calc. for C$_{17}$H$_{27}$NO$_6$.½H$_2$O:
  C 58.27  H 8.05  N 4.00
 found C 58.48  H 8.09  N 4.08

EXAMPLE 2

Preparation of Dihtdroqinghaosu-Benzenecarbamate

A solution of dihydroqinghaosu (142 mg, 0.5 mmol) in dry CH$_2$Cl$_2$ (6 ml) and phenyl isocyanate (60 mg, 0.5 mmol) was refluxed for ca. 2 days. The solution was filtered in vacuo at 40° C. to give an oil, which was chromatographed on a silica-gel column with petroleum ether/AcOEt 9:1. After evaporation of the solution, the white powder was recrystallized from (i-Pr)$_2$O to afford dihydroqinghaosu-benzendcarbamate (167 mg).

m.p. 110–113° C.; [α]$_D^{22}$ = +11.78° (C = 0.85, CHCl$_3$);
UV. 250 (4.40);
IR (KBr): 3315 (NH), 2932, 2875, 1728 (carbamate), 870, 845, 820 (peroxide), 742, 684 (aromatics)
$^1$H NMR (CDCl$_3$) δ (ppm)
5.49 (s, 1H, C$_5$—H)
5.78 (d, 1H, J=6.3, C$_{12}$—H)
2.36 (m, 1H, C$_{11}$—H)
MS (CI, NH$_3$), 404 (M$^+$+ 1)
Anal. Calc. for C$_{22}$H$_{29}$NO$_6$:
  C 65.49  H 7.24  N 3.47
 found C 65.34  H 7.85  N 3.39

EXAMPLE 3

Preparation of Dihydroqinghaosu-P-Nitrobenzenecarbamate.

A solution of dihydroqinghaosu (142 mg, 0.5 mmol) in dry CH$_2$Cl$_2$ (10 ml) was reacted with p-nitrophenyl isocyanate (123 mg, 0.75 mmol). Chromatography on silica gel with petroleum ether/AcOEt 9:1 afforded title compound (120 mg) as a white powder.

[α]$^{22}_D$=+5.31° (C=1.4, CHCl$_3$);
IR (KBr): 3300 (NH), 2925, 2870, 1742 (carbamate), 1540, 1330 (NO$_2$), 845 (peroxide), 740, 680 (aromatics) UV. 132 (4.26);
$^1$H NMR (CDCl$_3$) δ (ppm) 5.57 (s, 1H, C$_5$-H) 5.79 (d, 1H, C$_{12}$-H) 2.66 (m, 1H, C$_{11}$-H)
MS (CI, NH$_3$), 449 (M$^+$+1)

EXAMPLE 4

Preparation of Dihydroqinghaosu-M-Nitrobenzenecarbamate

The title compound was similarly prepared from dihydroqinghaosu and m-nitrophenyl isocyanate as Example 3.
m.p. 143°–145° C., UV: 242 (4.09)

EXAMPLE 5

Prepartion of Dihydroqinghaosu-O-Nitrobenzenecarbamate

The title compound was similarly prepared from dihydroqinghaosu and o-nitrophenyl isocyanate as Example 3.
m.p. 157–159° C., UV: 242 (4.06).

INDUSTRIAL APPLICATION

Compounds according to the present invention can be used to prepare agents for prevention and treatment of AIDS and drugs against malaria and toxoplasmosis.

We claim:

1. A compound represented by general formula (I) and its pharmaceutical acceptable salt,

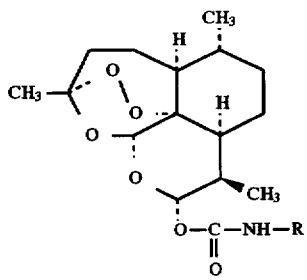

(I)

wherein R is selected from the group consisting of $C_1$–$C_4$ alkyl, phenyl substituted by a halogen atom, biphenyl unsubstituted or substituted by a halogen atom or a nitro group, and naphthyl unsubstituted or substituted by a halogen atom or a nitro group.

2. The compound of claim 1, wherein the compound is dihydroqinghaosu-methylcarbamate.

3. The compound of claim 1, wherein the compound is dihydroqinghaosu-ethylcarbamate.

4. The compound of claim 1, wherein the compound is dihydroqinghaosu-n-propylcarbamate.

5. The compound of claim 1, wherein the compound is dihydroqinghaosu-n-butylcarbamate.

6. The compound of claim 1, wherein the compound is dihydroqinghaosu-3-chlorobenzenecarbamate.

7. The compound of claim 1, wherein the compound is dihydroqinghaosu-4-chlorobenzenecarbamate.

8. The compound of claim 1, wherein the compound is dihydroqinghaosu-4-bromobenzenecarbamate.

9. The compound of claim 1, wherein the compound is dihydroqinghaosu-p-biphenylcarbamate.

10. The compound of claim 1, wherein the compound is dihydroqinghaosu-1-naphthylcarbamate.

11. A process for preparation of compounds represented by general formula (I) of claim 1, said process comprising:

adding isocyanates into dihydroqinghaosu dissolved in dichloromethane, with the molar ratio (mol/mol) of dihydroqinghaosu to isocyanates being 1:1 to 1:2, to obtain a reaction solution;

refluxing the reaction solution for 1–3 days with stirring;

filtering and evaporating the reaction solution to obtain a solid product;

chromatographing the solid product on a silica gel column by using a mixture of petroleumether and ethylacetate with a volume ratio of petroleumether to ethylacetate being 5:5–9:1; and collecting the required fraction, removing solvent and obtaining crystals.

12. A pharmaceutical composition containing the compound of claim 1.

13. An application for the compound represented by general formula (I) and its pharmaceutical acceptable salt in preparation of agents for prevention and treatment of AIDS.

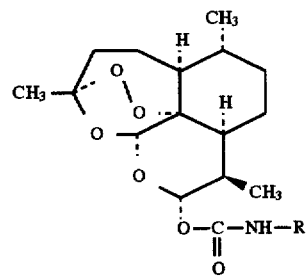

(I)

wherein R is selected from the group consisting of $C_1$–$C_4$ alkyl, $C_3$–$C_6$ cycloalkyl, phenyl unsubstituted or substituted by a halogen atom, phenyl substituted by an ortho or a meta nitro group, biphenyl unsubstituted or substituted by a halogen atom or a nitro group, and naphthyl unsubstituted or substituted by a halogen atom or a nitro group.

14. An application for the compound represented by general formula (I) and its pharmaceutical acceptable salt in preparation of antimalaria agents,

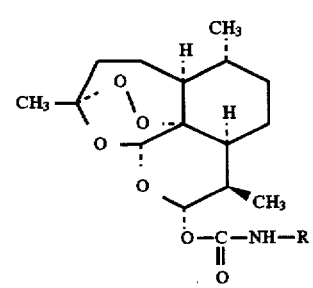

(I)

wherein R is selected from the group consisting of $C_1$–$C_4$ alkyl, $C_3$–$C_6$ cycloalkyl, phenyl unsubstituted or substituted by a halogen atom, biphenyl unsubstituted or substituted by a halogen atom or a nitro group, and naphthyl unsubstituted or substituted by a halogen atom or a nitro group.

15. An application for the compound represented by general formula (I) and its pharmaceutical acceptable salt in preparation of agents against toxoplasmosis,

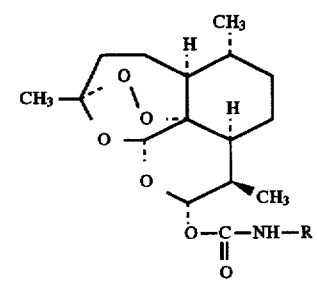

(I)

wherein R is selected from the group consisting of $C_1$–$C_4$ alkyl, $C_3$–$C_6$ cycloalkyl, phenyl unsubstituted or substituted by a halogen atom, phenyl substituted by an ortho or a meta nitro group, biphenyl unsubstituted or substituted by a halogen atom or a nitro group, and naphthyl unsubstituted or substituted by a halogen atom or a nitro group.

* * * * *